United States Patent
Biedermann et al.

(10) Patent No.: US 9,532,824 B2
(45) Date of Patent: Jan. 3, 2017

(54) CRIMPING TOOL

(71) Applicant: Biedermann Technologies GmbH & Co. KG, Donaueschingen (DE)

(72) Inventors: Lutz Biedermann, VS-Villingen (DE); Gerhard Pohl, St. Georgen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 841 days.

(21) Appl. No.: 13/628,343

(22) Filed: Sep. 27, 2012

(65) Prior Publication Data

US 2013/0079831 A1 Mar. 28, 2013

Related U.S. Application Data

(60) Provisional application No. 61/540,242, filed on Sep. 28, 2011.

(30) Foreign Application Priority Data

Sep. 28, 2011 (EP) .................................... 11183203

(51) Int. Cl.
| | | |
|---|---|---|
| A61B 17/86 | (2006.01) | |
| A61B 17/88 | (2006.01) | |
| A61B 17/70 | (2006.01) | |

(52) U.S. Cl.
CPC ....... *A61B 17/8863* (2013.01); *A61B 17/7037* (2013.01)

(58) Field of Classification Search
CPC . A61B 17/84; A61B 17/7035; A61B 17/7032; A61B 17/7037; A61B 17/7038; A61B 17/7049; A61B 17/705; A61B 17/8863
USPC ...... 606/246–279, 300–331; 29/237; 72/397, 72/409.19, 402; 81/309; 470/5, 51
See application file for complete search history.

(56) References Cited

U.S. PATENT DOCUMENTS

| | | | | |
|---|---|---|---|---|
| 4,982,594 A | * | 1/1991 | Wiebe | H01R 43/04 72/409.14 |
| 5,261,913 A | | 11/1993 | Marnay | |
| 5,350,373 A | * | 9/1994 | Colligan | A61B 17/06004 606/1 |
| 5,716,356 A | | 2/1998 | Biedermann et al. | |
| 5,934,136 A | * | 8/1999 | Bracher | B25B 27/146 29/751 |
| 6,293,004 B1 | * | 9/2001 | Holliday | B25B 27/10 29/751 |
| 7,318,272 B1 | * | 1/2008 | Steiner | B25B 7/02 29/750 |
| 2004/0079132 A1 | * | 4/2004 | Frenken | B21D 39/048 72/402 |

(Continued)

OTHER PUBLICATIONS

Extended European Search Report dated Mar. 12, 2012 for Application No. 11183203.6-1526, 6 sheets.

*Primary Examiner* — Todd E Manahan
*Assistant Examiner* — Marcela I Shirsat
(74) *Attorney, Agent, or Firm* — Lewis Roca Rothgerber Christie LLP

(57) ABSTRACT

A crimping tool for producing a polyaxial bone anchoring device (1, 1') is provided. The crimping tool includes at least one tip holder having a crimping tip and an inclined passage and an actuating member having at least an inclined leg, wherein the inclination of the inclined passage corresponds to the inclination of the inclined leg.

23 Claims, 13 Drawing Sheets

(56) References Cited

U.S. PATENT DOCUMENTS

| | | | |
|---|---|---|---|
| 2005/0049586 A1* | 3/2005 | Daniel | A61B 18/148 606/41 |
| 2008/0295565 A1* | 12/2008 | Boemmels | G02B 6/3855 72/416 |
| 2010/0094306 A1 | 4/2010 | Chang et al. | |
| 2010/0211114 A1 | 8/2010 | Jackson | |

* cited by examiner

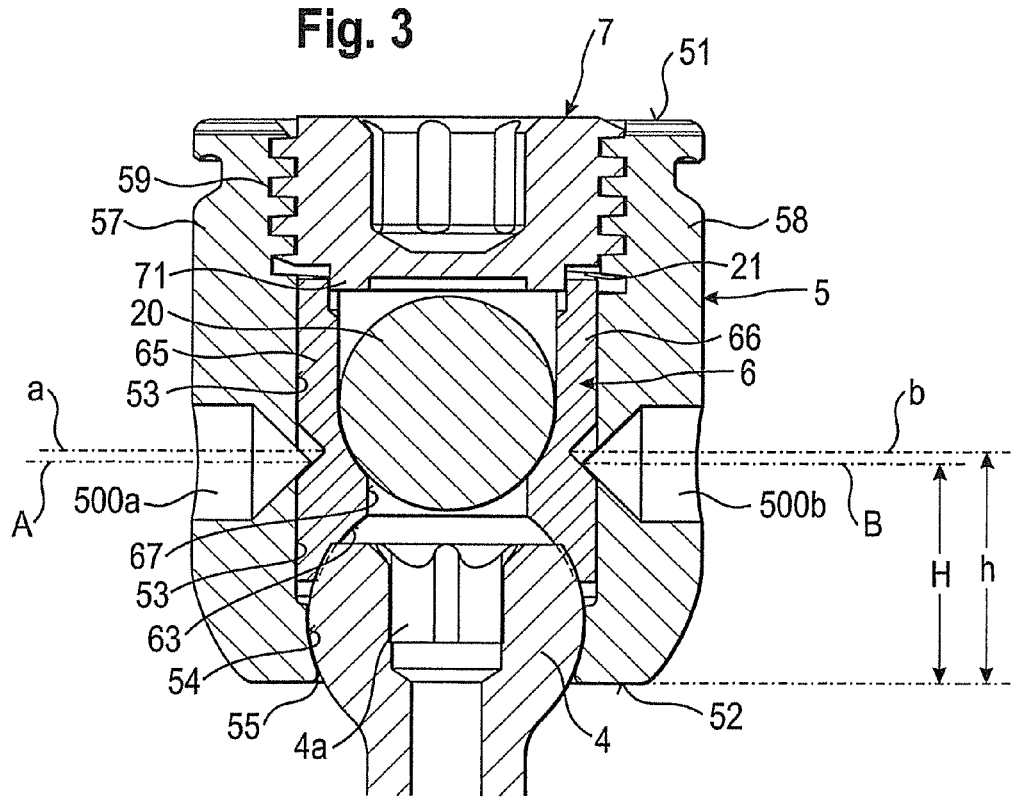

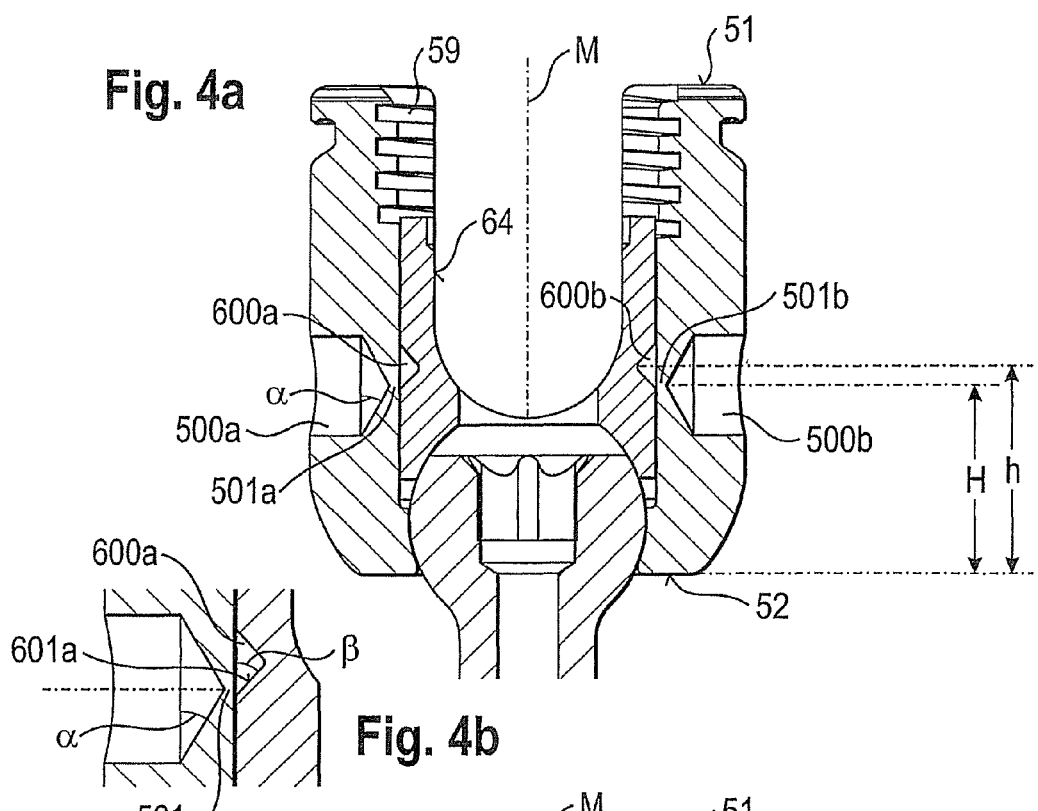
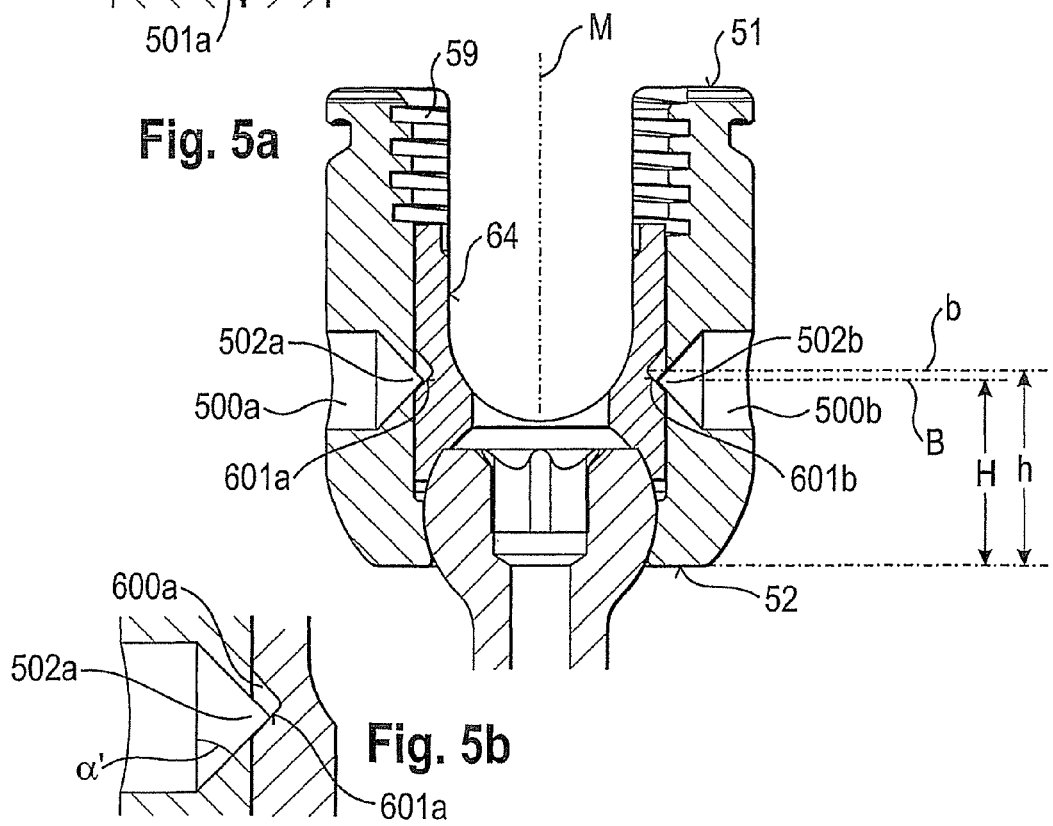

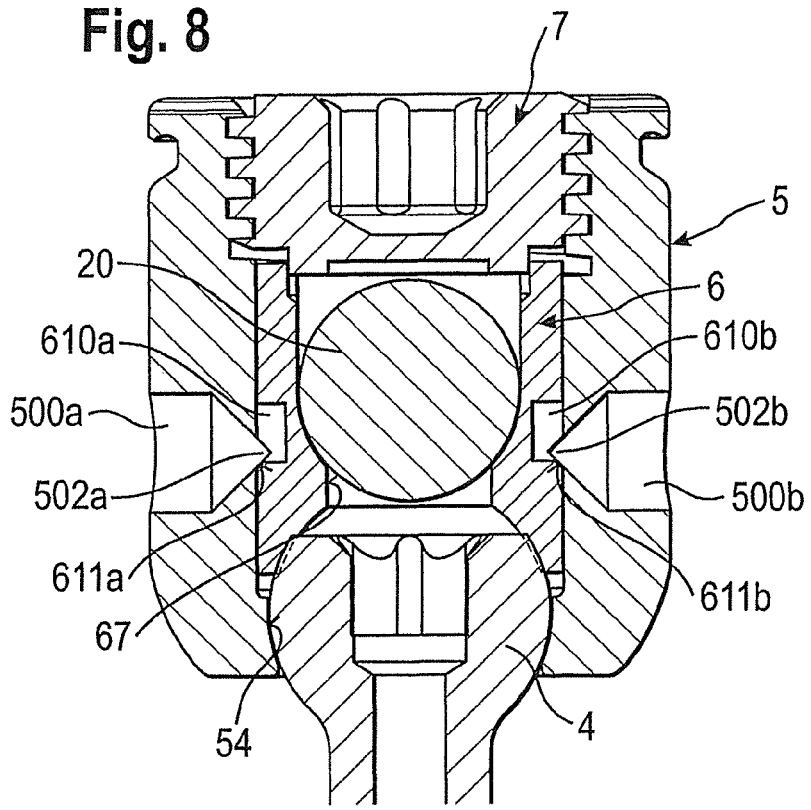
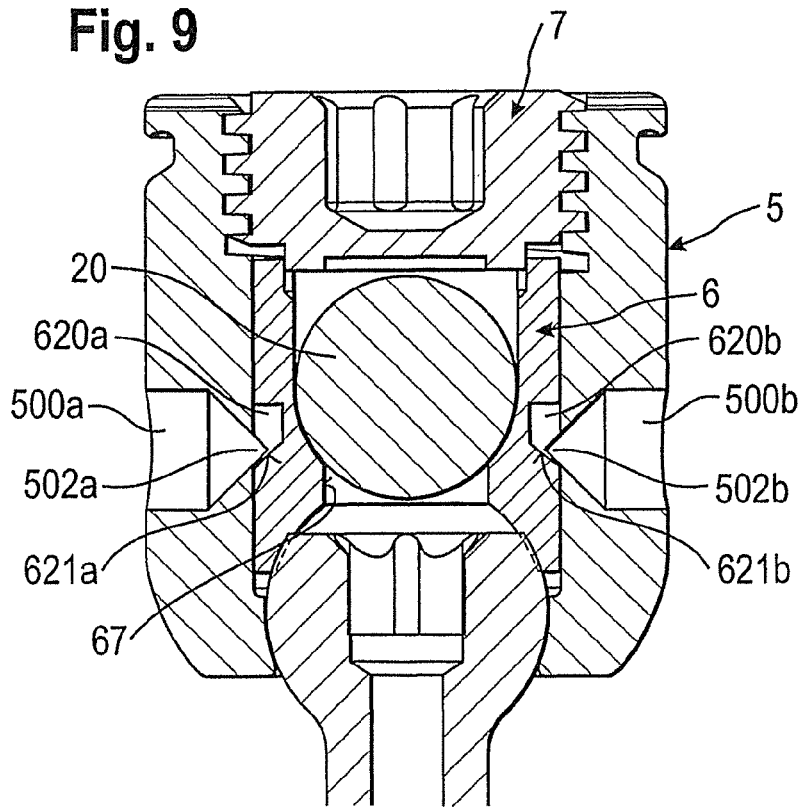

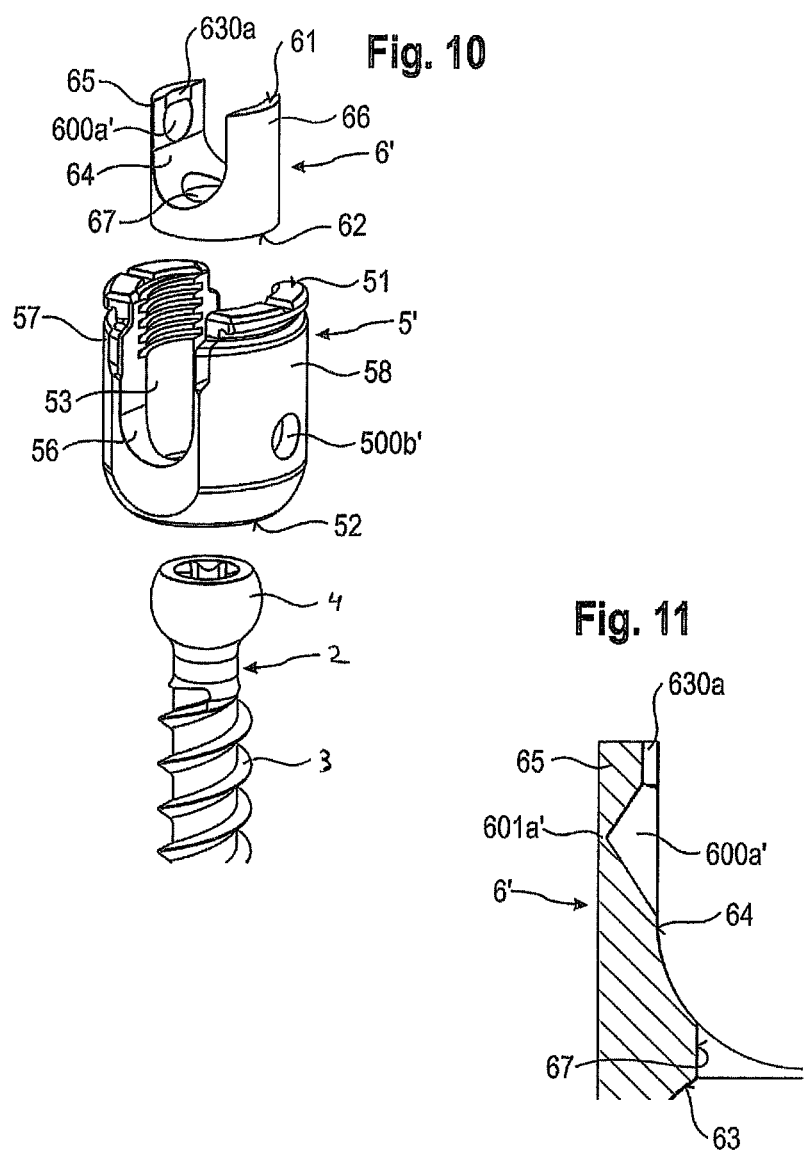

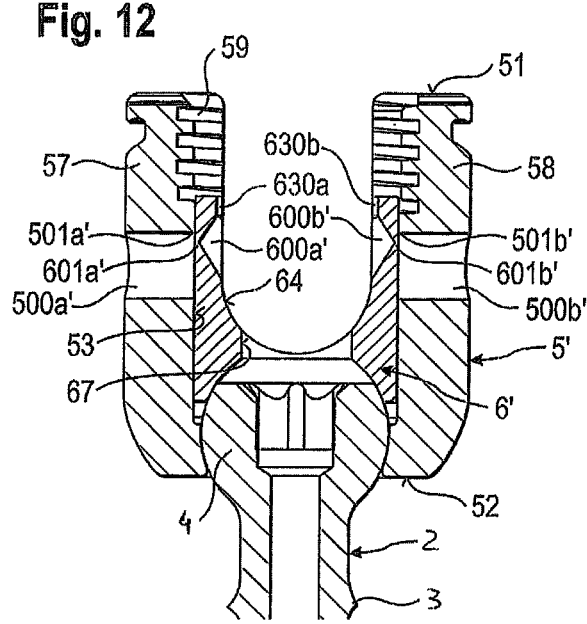
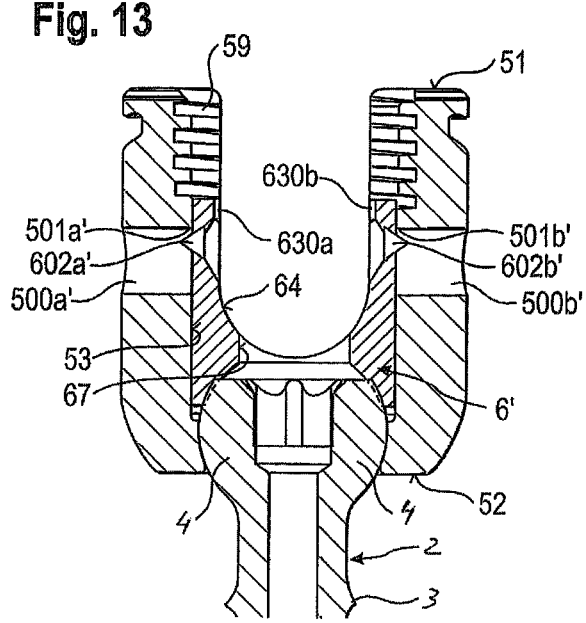

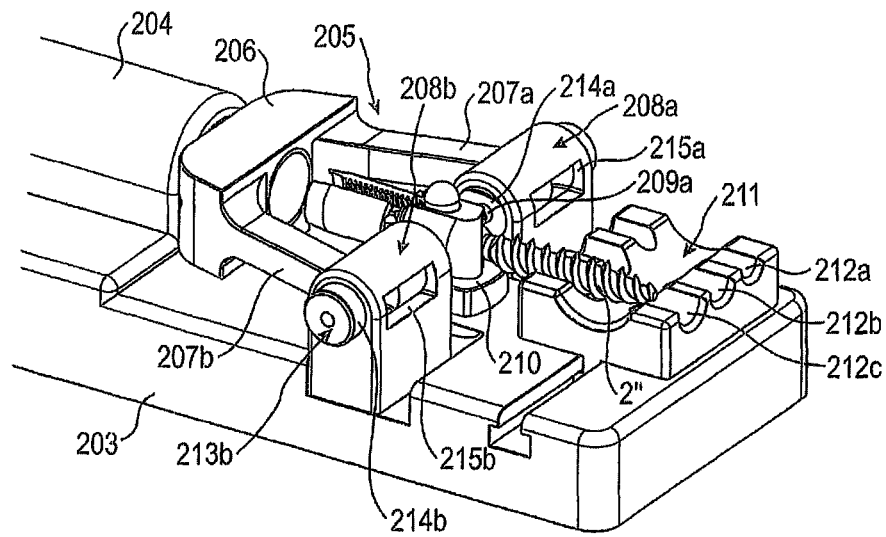
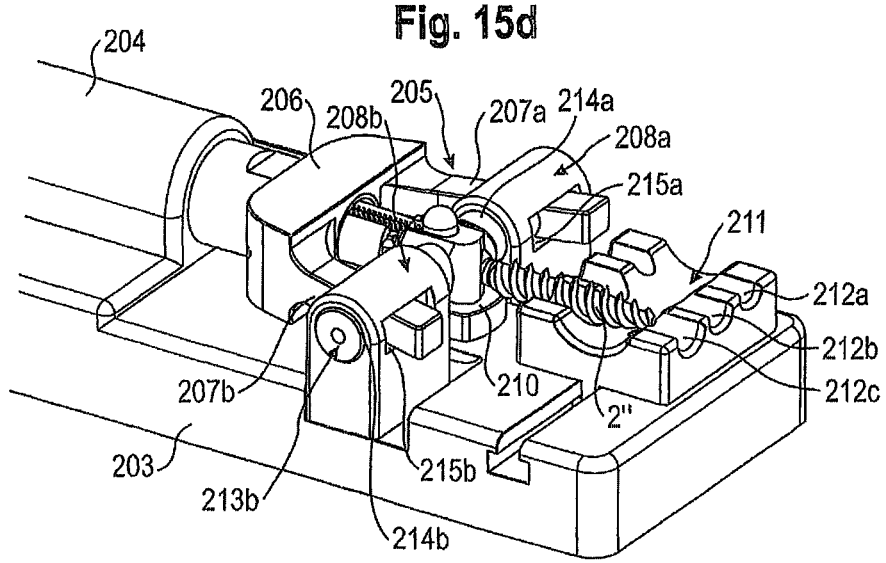

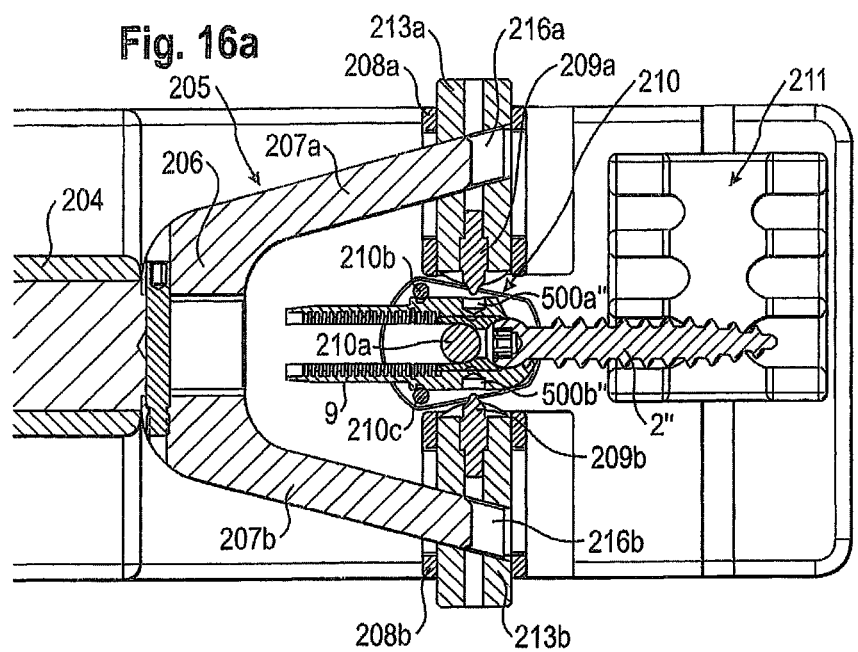
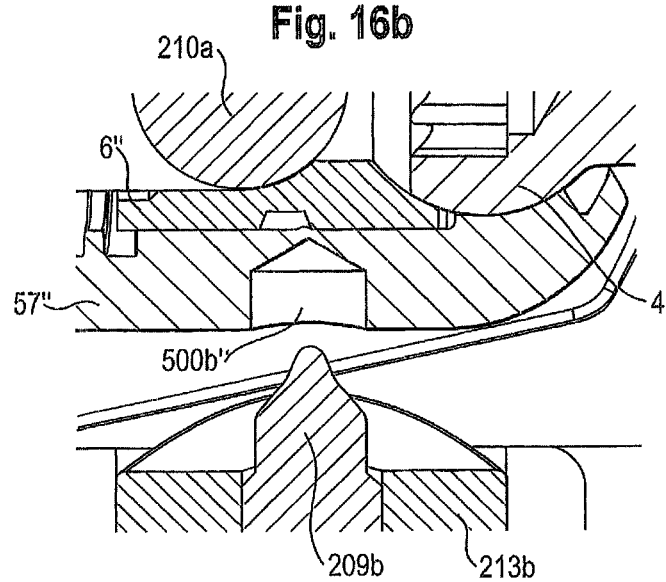

CRIMPING TOOL

CROSS-REFERENCE TO RELATED APPLICATION(S)

The present application claims the benefit of U.S. Provisional Patent Application Ser. No. 61/540,242, filed Sep. 28, 2011, the contents of which are hereby incorporated by reference in their entirety, and claims priority to European Patent Application EP 11 183 203.6, filed Sep. 28, 2011, the contents of which are hereby incorporated by reference in their entirety.

FIELD OF THE INVENTION

The invention relates to a crimping tool for producing a polyaxial bone anchoring device that comprises at least one tip holder having a crimping tip and an inclined passage and an actuating member having at least an inclined leg, wherein the inclination of the inclined passage corresponds to the inclination of the inclined leg.

BACKGROUND OF THE INVENTION

U.S. Pat. No. 5,716,356 describes a polyaxial bone screw including a screw element and a receiving part which is pivotably connected to the screw element and a pressure element to exert pressure onto the head of the screw element to lock the angle between the screw element and the receiving part. The receiving part has a U-shaped channel for receiving a stabilization rod. The pressure element comprises a cylindrical recess, which is to be aligned with the U-shaped channel to receive the rod therein. In order to hold the pressure element in a position aligned with the U-shaped channel, the position of the pressure element is fixed by crimping through bores provided in the receiving part.

When the head of the bone anchoring element is freely pivotable with respect to the receiving part before locking the head in a final angular position, the alignment of the receiving part and the insertion of the rod may be difficult in more complex clinical applications, for example, when a multitude of bone anchors have to be connected to the rod.

SUMMARY

It is an object of the invention to provide a crimping tool for producing a polyaxial bone anchoring device, which allows improved handling.

With the crimping tool a temporary clamping of the head of the polyaxial bone anchoring device in a desired angular position with respect to the receiving part without locking the head can be achieved. This allows maintenance of the receiving part in an adjustable angular position. In this condition, the pressure element exerts a preload onto the head in which the head is not locked but prevented from freely pivoting. When the head is temporarily clamped, the alignment of the receiving part with respect to the rod and the insertion of the rod is facilitated, in particular in a situation in which a multitude of bone anchors have to be connected to the rod.

The polyaxial bone anchoring device and also the crimping tool comprises only few parts which are of simple design. The mechanism to frictionally maintain the head before locking it is free from any spring members or portions. This facilitates the manufacturing of the polyaxial bone anchoring device. Furthermore, existing receiving parts and pressure elements can be used without having to redesign their shape. It is possible to simply change the location of the crimp bores.

The amount of preload exerted onto the head by the pressure member can be exactly predefined in a simple manner by selecting the position and shape of the crimp bores. The polyaxial bone anchoring device is provided to the surgeon in a pre-assembled manner, in which the pressure element is axially and rotationally fixed to such an extent that it can not fall out or be rotated out of its aligned position. This allows a safe handling by the surgeon.

By the crimping tool a one-step crimping operation can be realized whereby high friction between the pressure element, the screw head and the seat of the screw head in the receiving part can be achieved without completely locking the bone anchoring device. A polyaxial movement of the screw referring to the receiving part is still possible. The construction of the tool is robust and the crimping procedure is simple. This allows an improved handling by the surgeon.

BRIEF DESCRIPTION OF THE DRAWINGS

Further features and advantages of the invention will become apparent from the description of embodiments by means of the accompanying drawings.

In the drawings:

FIG. 3 shows a cross-sectional view of the polyaxial bone anchoring device of FIG. 1 in an assembled state before final locking of the head.

FIG. 4a shows a cross-sectional view of the polyaxial bone anchoring device of FIG. 1 before provisionally fixing the pressure element in the receiving part.

FIG. 4b shows an enlarged portion of FIG. 4a.

FIG. 5a shows a cross-sectional view of the polyaxial bone anchoring device of FIG. 1 in the pre-assembled state after provisionally fixing of the pressure element in the receiving part.

FIG. 5b shows an enlarged portion of FIG. 5a.

FIG. 8 shows a cross-sectional view of a modified embodiment of the polyaxial bone anchoring device before locking of the head.

FIG. 9 shows a cross-sectional view of a further modified embodiment of the polyaxial bone anchoring device in a state before locking of the head.

FIG. 10 shows a perspective exploded view of a second embodiment of the polyaxial bone anchoring device.

FIG. 11 shows an enlarged cross-sectional view of a portion of the pressure element of the bone anchoring device of FIG. 10.

FIG. 12 shows a cross-sectional view of the polyaxial bone anchoring device of FIG. 10 before provisionally fixing the pressure element in the receiving part.

FIG. 13 shows a cross-sectional view of the polyaxial bone anchoring device of FIG. 12 in the pre-assembled state after provisionally fixing of the pressure element in the receiving part.

FIG. 15c shows a perspective view of the tool according to FIG. 14a in the starting position with inserted bone anchoring device.

FIG. 15d shows a perspective view of the tool according to FIG. 14a in the crimping position.

FIG. 16a shows a cross-sectional view of the tool according to FIG. 14a in the starting position.

FIG. 16b shows an enlarged portion of FIG. 16a.

FIG. 17b shows an enlarged portion of FIG. 17a.

FIG. 18b shows an enlarged portion of FIG. 18a.

DETAILED DESCRIPTION

Figure 1:
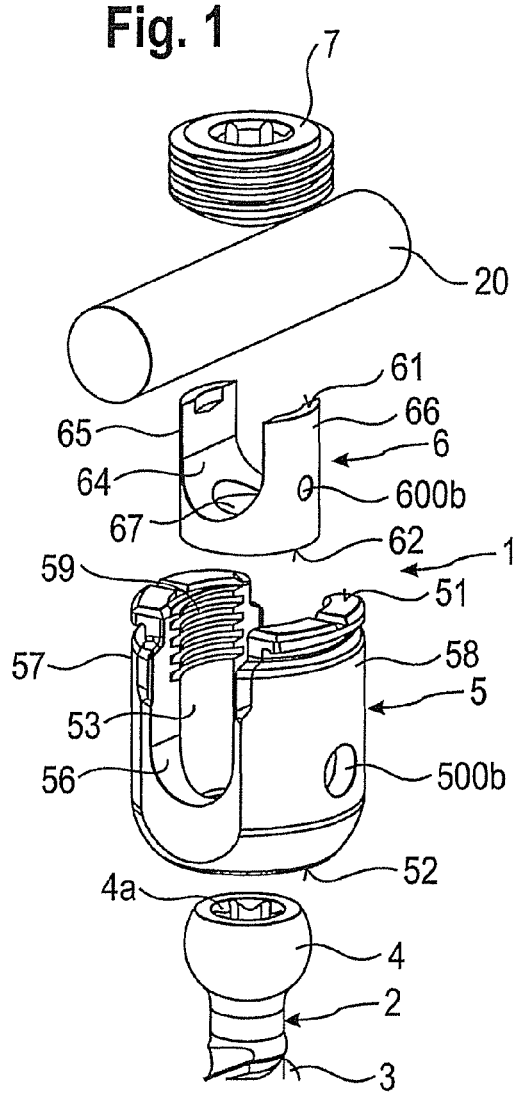
FIG. 1 shows a perspective exploded view of the polyaxial bone anchoring device according to a first embodiment.
Figure 2:
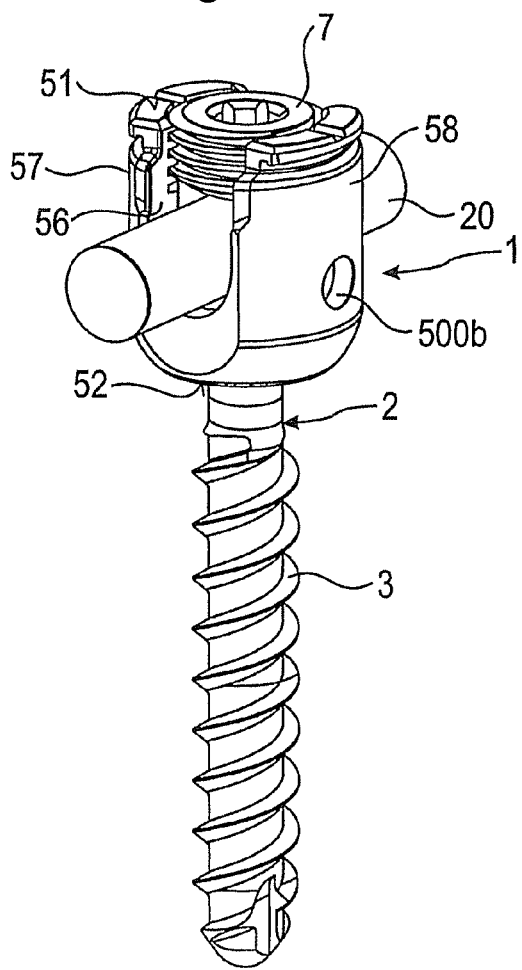
FIG. 2 shows the polyaxial bone anchoring device of FIG. 1 in an assembled state.
Figure 6:
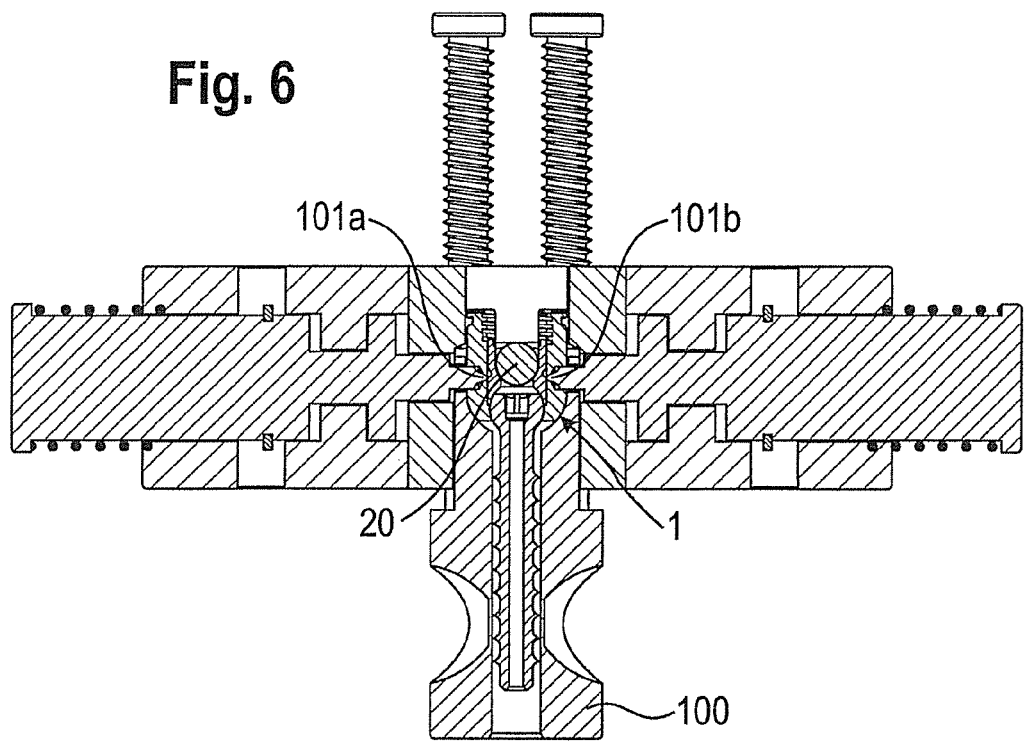
FIG. 6 shows a cross-sectional view of a tool for provisionally fixing the pressure element in the receiving part.
Figure 7:
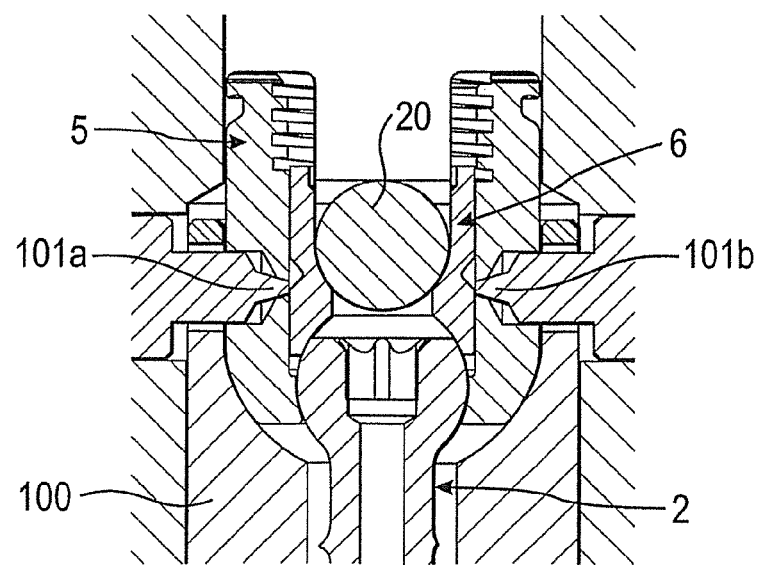
FIG. 7 shows an enlarged portion of FIG. 6.
Figure 14A:
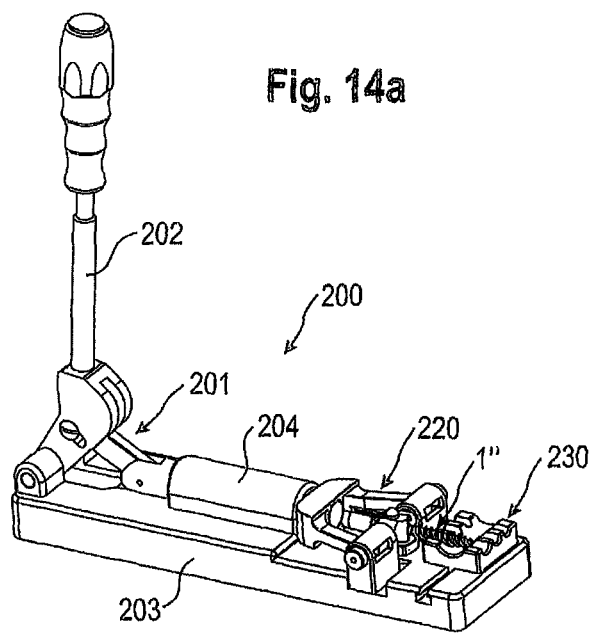
FIG. 14a shows a perspective view of a tool for provisionally fixing the pressure element in the receiving part according to the bone anchoring device of FIG. 10 in a starting position.
Figure 14B:
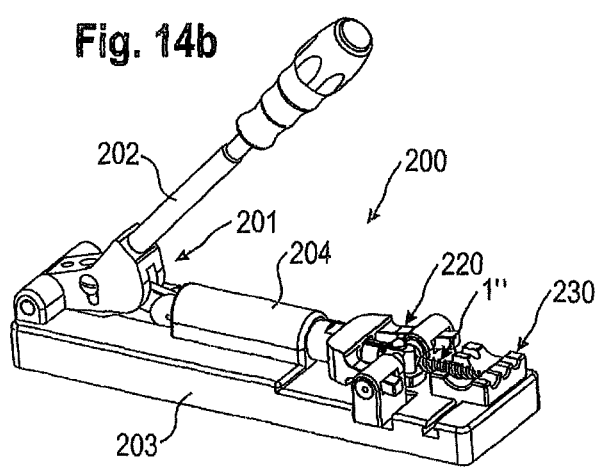
FIG. 14b shows a perspective view of the tool according to FIG. 14a in a crimping position.

The polyaxial bone anchoring device 1 according to a first embodiment as shown in FIGS. 1 to 3 includes a bone anchoring element in the form of a screw member 2 having a threaded shaft 3 and a head 4. The head 4 is generally spherical and includes a recess 4a at its free end for engagement with a tool to insert the threaded shaft 3 into bone. The bone anchoring device further includes a receiving part 5 for connecting the screw member 2 to a rod 20. A pressure element 6 is arranged in the receiving part on top of the head 4. For securing the rod 20 in the receiving part and for exerting pressure onto the head, a locking device, for example an inner screw 7, which cooperates with the receiving part 5, is provided.

The receiving part is a substantially cylindrical one piece part and has a top end 51 and a bottom end 52. A passageway extending from the top end to the bottom end is formed by a coaxial bore 53 followed by a seat portion 54 for receiving the head 4 of the screw member 2. The seat portion 54 has an opening 55 at the bottom end 52 through which the shaft 3 of the screw member extends. The seat portion 54 is shown to be spherically-shaped, but it can be tapered or it can have any other shape that allows the head 4 to be received so that it can pivot with respect to the receiving part 5. At the top end 51 a substantially U-shaped recess 56 is provided by means of which two free legs 57, 58 are formed that are the sidewalls of a channel for receiving the rod 20. An internal thread 59 is provided at the legs for cooperating with the inner screw 7.

The pressure element 6 is formed in one piece. It is of substantially cylindrical construction and has an outer diameter, which allows it to move in the axial direction within the bore 53 of the receiving part 5. The pressure element 6 has a top end 61 and a bottom end 62. When the pressure element is inserted into the receiving part, the bottom end 62 faces the head 4 of the screw element 2. At the bottom end 62 a spherical recess 63 is provided, which is adapted to the size and shape of the head 4. The spherical recess is configured to come into frictional engagement with the spherical surface of the head. At the top end 61, a U-shaped recess 64 is provided by means of which two free legs 65, 66 are formed that form a channel to receive the rod 20 therein. Furthermore, the pressure element 6 includes a coaxial bore 67 for accessing the screw head 4 with a tool (not shown). As shown in FIGS. 1 and 3, the pressure element 6 is a solid member without any spring portions that could render it flexible. It is arranged in the receiving part such that the U-shaped recess 56 of the receiving part 5 and the U-shaped recess 64 of the pressure element are aligned.

In the assembled state as shown in FIG. 3, the screw head 4 is located in the seat 54 and the pressure element 6 is arranged on top of the screw head 4. The height of the free legs 65, 66 of the pressure element is configured such that the free legs 65, 66 extend above the rod 20 when the rod is inserted and rests on the bottom of the channel.

The locking device in the form of the inner screw 7 has a projection 71 extending into the channel formed by the free legs 65, 66 of the pressure element 6. The size of the projection 71 in an axial direction is such that when the inner screw 7 is tightened, the projection 71 presses onto the rod while there is still a gap 21 between the top end 61 of the pressure element and the lower side of the inner screw 7. Therefore, with the single inner screw 7, pressure can be exerted onto the rod 20 only, which in turn can exert pressure onto the pressure element 6. It should be noted that instead of the single part locking device in form of the inner screw 7 a two-part locking device can be used (not shown). The two-part locking device includes a first part to be screwed in-between the legs 57, 58 of the receiving part. The first part presses onto the top end 61 of the pressure element 6. Further, a second part in form of an inner screw is provided in the first part, which presses onto the rod 20. By means of this, the head 4 and the rod 5 can be independently fixed.

The pressure element 6 is retained in the receiving part 5 as shown in FIGS. 3 to 5. As shown in particular in 4a and 4b, the receiving part includes two blind holes 500a, 500b forming crimp bores that extend from the outer surface to a distance from the inner wall of the coaxial bore 53. The blind holes 500a, 500b are arranged at 180° offset from each other and at 90° with respect to the channel formed by the U-shaped recess 56. The blind holes 500a, 500b are aligned perpendicular with respect to the bore axis M of the coaxial bore 53. At their end they are tapered with an angle α preferably less than 45°, for example 22.5°, with respect to an axis parallel to the bore axis M. The bore axes A and B of the blind holes 500a, 500b are provided at a distance H from the second end 52 of the receiving part.

The portions of the receiving part that are between the closed ends of the blind holes 500a, 500b and the coaxial bore 53 of the receiving part are configured to be deformable portions 501a, 501b.

The pressure element 6 correspondingly includes two recesses 600a, 600b which are 180° offset from each other and 90° offset from the channel formed by the U-shaped recess 64. The recesses 600a, 600b have a center axis a, b, respectively, which is perpendicular to the bore axis M. In the embodiment shown, the recesses 600a, 600b have a conical shape. The downwardly extending flanks 601a, 601b of the recesses 600a, 600b each include an angle β of approximately 45° with the central bore axis M. As shown in FIGS. 4a and 4b, when the pressure element 6 is inserted such that it rests on the head 4 of the screw element, the central axis a, b of the recesses 600a, 600b has a distance h from the second end 52 of the receiving part 5 that is greater than the distance H of the central axis A, B of the blind holes 500a, 500b. In other words, the recesses 600a, 600b are arranged above the blind holes 500a, 500b.

The distance between the recesses and the blind holes is such that when the deformable portions 501a, 501b are deformed by applying a force via for example, a crimping tool to the blind holes 500a, 500b, the deformed material protrudes from the inner wall of the receiving part and presses onto the lower flanks 601a, 601b of the recesses 600a, 600b, respectively, to exert a downward force onto the pressure element 6. As shown in FIGS. 5a and 5b, deforming the deformable portions 5a, 5b results in deformed portions 502a, 502b which exert pressure on the lower flank 601a, 601b of the recesses 600a, 600b of the pressure element 6. For example, after deformation, the angle α is approximately 45°, which is approximately the same as the angle of the lower flank 601a, 601b. The blind holes 500a, 500b with their respective deformable portions 501a, 501b and the recesses 600a, 600b are constructed such that by deforming the deformable portions 501a, 501b into deformed portions 502a, 502b which engage the recesses 600a, 600b, the resulting force onto the pressure element 6 generates a preload onto the head 4, which clamps the head by means of friction. By selecting the sizes of blind holes and the recesses and their position, a desired friction force can be achieved. By this friction force the head can be maintained in a desired angular position and can be moved out of this position by applying a force greater than the friction force either to the screw element or to the receiving part. Simultaneously, the pressure element 6 is secured against rotation and secured against escaping through the top end 51 of the receiving part 5. The recesses 600a, 600b provide space for accommodating a part of the deformed material. Also, the recesses 600a, 600b provide space for the deformed portions 502a, 502b when the pressure element 6 moves downward to finally lock the head.

A method for manufacturing the polyaxial bone anchoring device is explained with reference to FIGS. 4a, 4b, 5a, 5b, 6 and 7. A crimping tool shown in FIGS. 6 and 7 generally comprises a holder 100 for the bone anchoring device, which serves for fixing the receiving part 5 with inserted screw element 2 and pressure element 6 as it is shown in FIGS. 4a and 4b. The rod 20 may be inserted for providing a counterforce to avoid deformation of the free legs 65, 66 of the pressure element. The crimping tool further includes two crimping tips 101a, 101b, which are arranged 180° offset from each other and are dimensioned to be introduced into the blind holes 500a, 500b and to deform the deformable portions 501a, 501b, so that the displaced material, which forms the deformed portions 502a, 502b, engages the recesses 600a, 600b of the pressure element. As can be seen in particular in FIG. 7, the crimping tips 101a, 101b have an angle which is more acute than that of the bottom of the blind hole 500a, 500b. The crimping tips 101a, 101b deform the deformable parts 501a, 501b such that the deformed portions 502a, 502b press onto the lower flanks 601a, 601b of the recesses 600a, 600b, respectively. Thereafter, the crimping tips 101a, 101b are retracted. The crimping process can be force-actuated and/or path-controlled.

After the crimping tips 101a, 101b are retracted, the polyaxial anchoring device can be removed from the holder 100. The polyaxial bone anchoring device is then in a pre-assembled state with the screw element 2 being inserted and the pressure element 6 being held in such a way that it exerts a slight preload onto the head 4, which frictionally holds the head in an angular position.

It shall be noted that the shape of the blind holes may vary. In particular, the angle of the conical bottom may vary or the bottom may have a rounded or other shape. The recesses provided at the pressure element 6 may also have a different shape. As shown in FIG. 8, the recesses 610a, 610b can have, for example, a substantially rectangular cross-section. A lower side of the recess may comprise an inclined edge 611a, 611b for engagement with the deformed portions 502a, 502b.

As shown in FIG. 9, the cross-section of the recesses 620a, 620b of the pressure element can be for example trapezoidal, with an inclined lower flank 621a, 621b for engagement with the deformed portions 502a, 502b.

All parts of the bone anchoring device are made of a body-compatible material, such as a body-compatible metal, for example, titanium, body-compatible metal alloys such as, for example, Nitinol or from a body-compatible plastic material, such as, for example, polyether ether ketone (PEEK) or combinations thereof.

Usually, several bone anchoring devices are necessary for stabilizing bone parts or vertebrae with the rod. In use, the bone anchoring devices are pre-assembled as shown in FIGS. 5a and 5b. The screw members are screwed into the bone or a vertebra. Then, the receiving parts are pivoted by applying a force greater than the friction force until each receiving part has the correct orientation for the insertion of the rod. Due to the friction force, each receiving part is held in this angular position. Thereafter, the rod, which connects the bone anchoring devices, is inserted and the inner screw is tightened to move the pressure element downwards to lock the head in the seat so that the angular position of the screw member with respect to the receiving part is fixed. The rod is simultaneously fixed by the inner screw. Since the deformed portions 502a, 502b engage only the lower flank of the recesses provided at the pressure element, the recesses provide enough space for the deformed portions to allow a downward movement of the pressure element.

Further modifications of the previously described embodiment are conceivable. For example, only one deformed portion at the receiving part and one corresponding recess at the pressure element is sufficient. However, more than two deformed portions and corresponding recesses can also be provided.

A second embodiment of the bone anchoring device is described with reference to FIGS. 10 to 13. Parts or portions that are identical or similar to the previously described embodiment are designated with the same reference numerals and the description thereof will not be repeated. The second embodiment differs from the first embodiment mainly in that the functions of the pressure element and the receiving part with respect to the provisional fixation with preload onto the head are reversed.

As can be seen in FIG. 10, the receiving part 5' has instead of the blind holes 500a, 500b two through holes 500a', 500b'. Although recesses at the inner wall of the receiving part instead of through holes would be sufficient, providing through holes is easier to manufacture and allows upgrading of existing receiving parts that have the blind holes of the first embodiment.

The pressure element 6' has two recesses 600a', 600b', arranged offset by 180°, that extend from the inner wall of the channel 64 into the legs 65, 66, respectively. The recesses can have a substantially triangular cross-section with a taper of approximately 22.5°, similar to that of the blind holes 500a, 500b of the receiving part of the first embodiment. At the upper edge of the recesses, a rectangular recess 630a, 630b is provided, respectively, the depth of which is smaller than that of the recesses 600a', 600b'. The recesses 630a, 630b are optional and may facilitate the insertion of a crimping tool.

Between the outer surface of the pressure element 6' and the bottom of the recesses 600a', 600b', deformable portions 601a', 601b' are formed that can be deformed into deformed portions 602a', 602b' as shown in FIG. 13. In the pre-assembled and non-deformed state, as shown in FIG. 12, the pressure element 6' is situated in the receiving part 5' in such a position that it rests on the head 4 and the deformable portions are slightly below the upper wall portion of the through holes 500a', 500b'. Then, crimping tips (not shown) are introduced into the recesses 600a', 600b' and the deformable portions 601a', 601b' are deformed towards the outside. The deformed portions 602a', 602b' abut against upper wall portions 501a', 501b' of the through holes 500a', 500b' at the inner side of the receiving part 5' as shown in FIG. 13. The deformed portions 602a', 602b' have then a taper of around 45°. When the deformed portions abut against the upper wall portions 501a', 501b' of the through holes 500a', 500b', a downward force is exerted onto the head 4, which clamps the head by friction.

The shape of the recesses and blind holes of the embodiments described is not limited to the tapered form. Also the angles of the taper are not limited to the values described. Other shapes are possible that also achieve a downwardly directed force when the deformable portions are deformed.

For the anchoring element, all kinds of anchoring elements can be used and combined with a receiving part. These anchoring elements are, e.g., screws of different lengths, screws of different diameters, cannulated screws, screws with different thread forms, nails, hooks, etc. The head and the shaft can be separate parts which are connectable to each other.

The shape of the receiving part is not limited to the embodiment shown. For example, the receiving part can have an asymmetric end portion for allowing a greater pivot angle of the screw member to one side. The seat for the head may be provided in an insert piece being part of the receiving part. Also, it is possible to have a recess allowing the rod to be introduced from the side instead of being introduced from the top or a closed recess through which the rod has to be guided. Various kinds of locking devices, including two- or more-part locking devices, outer nuts, outer caps, bayonet locking devices or others are possible.

In a further modification, the receiving part is configured to allow the introduction of the screw element from the bottom end.

FIGS. 14a to 18b show a second embodiment of a crimping tool 200 to be used for manufacturing the polyaxial bone anchoring device 1" which can be provided as a hand lever press. The bone anchoring device 1" shown in FIG. 15b differs from the bone anchoring device 1 described above in the shape of the receiving part 5". The other parts of the bone anchoring device 1" are the same as the parts referring to the first embodiment and the description thereof shall not be repeated. The receiving part 5" has an asymmetric bottom end 52" for allowing a greater pivot angle of the screw member to one side. Such asymmetric bottom end 52" can be achieved, for example, by cutting away a portion of the receiving part 5" at an inclined angle. Furthermore, the receiving part 5" is formed with a coaxial tube shaped extension 9 that has a slot 91 for inserting a rod and an internal thread 92. The extension 9 is used for minimally invasive surgery and can be broken away after tightening the inner locking screw. The crimping tool 200 can be applied to enhance the friction force between the pressure element 6" and the screw head 4" of the pre-assembled bone anchoring device. As can be seen from FIGS. 14a and 14b the tool 200 comprises a frame 203, a handle 202, a lever 201, a lever guiding member 204 for guiding the lever 201, a crimping device 220 and a shank holder 230. The lever 201 can be a knee lever, for example. The lever guiding member 204 can be fixedly connected to or formed integrally with the frame 203.

As can be seen from FIGS. 15a to 18b the crimping device 220 comprises an actuating element 205 having a base 206 and two legs 207a, 207b which are substantially parallel to the surface of the frame 203 and extend from the base 206 towards the shank holder 211 and wherein the legs 207a, 207b move away from each other, thereby forming a V-shaped construction together with the base 206. The crimping device 220 further comprises two tip guides 208a, 208b each having a tip holder 213a, 213b and a crimping tip 209a, 209b.

The crimping tip guides 208a, 208b are fixedly connected to or formed integrally with the frame 203 and each comprise a first cylindrical, in particular circular cylindrical, passage 214a, 214b and a second cuboidal passage 215a, 215b. The first passages 214a, 214b and the second passages 215a, 215b extend substantially parallel to the surface of the frame 203 and extend substantially perpendicular to each other. The second cuboidal passages 215a, 215b can also have another shape, for example be cylindrical.

The tip holders 213a, 213b are movably guided by the tip guides 208a, 208b in the first cylindrical passages 214a, 214b such that the crimping tip holders 213a, 213b having the crimping tips 209a, 209b are capable of moving towards each other for crimping the bone anchoring device 1'. As can be seen from FIGS. 16a to 18b, the tip holders 213a, 213b each comprise an inclined passage 216a, 216b, wherein the inclination of the inclined passage 216a, 216b corresponds to the inclination of the legs 207a, 207b. The inclined passages 216a, 216b extend substantially parallel to the surface of the frame 203 and are in line with the legs 207a, 207b. The legs 207a, 207b of the actuating element 205 are thereby movably guided by the tip guides 208a, 208b in the second cuboidal passages 215a, 215b such that legs 207a, 207b actuate the crimping tip holders 213a, 213b having the crimping tips 209a, 209b which are capable of moving towards each other for crimping the bone anchoring device 1'. The movement of the legs 207a, 207b only takes place in a horizontal direction. In the horizontal direction which is parallel to the surface of the frame 203, the second passages 215a, 215b are wider than the width of the legs 207a, 207b to allow them to be guided.

The crimping tips 209a, 209b are positioned within the crimping tip holders 213a, 213b, for example by a press-fit arrangement. The crimping tips 209a, 209b are arranged 180° offset from each other, pointing at each other and are dimensioned to be introduced into the blind holes 500a", 500b" of the bone anchoring device 1" and to deform the deformable portions, so that the displaced material, which forms the deformed portions, engages the recesses of the pressure element as described above. As can be seen in particular in FIG. 17b, the crimping tips 209a, 209b have an angle, which is more acute than that of the bottom of the blind hole 500a", 500b". The crimping tips 209a, 209b deform the deformable portion such that the deformed portion presses onto the lower flank of the recess, respectively as described above.

Furthermore, a receiving part holder 210 for holding and fixing the bone anchoring device 1" in operation is provided on the frame 203, wherein the receiving part holder 210 is located between the two tip guides 208a, 208b. The receiving part holder 210 is fixedly connected to or formed integrally with the frame 203 and comprises a first positioning pin 210a, a second positioning pin 210b and a third positioning pin 210c projecting from a bottom plate of the receiving part holder 210. The first positioning pin 210a is positioned substantially in the center of the receiving part holder 210 extending between the two free legs 57", 58" of the bone anchoring device 1" and thereby holding the bone anchoring device 1" in position in operation. The second and the third positioning pin 210b, 210c are positioned such that they contact the outer surface of the two free legs 57", 58", respectively and thereby additionally holding the bone anchoring device 1" in position in operation.

The shank holder 211 comprises a plurality of grooves 212a, 212b, 212c having different sizes referring to their width for supporting different sized shafts 2". The shank holder 211 is movably supported on the frame 203, wherein the shank holder 211 is able to move perpendicular to the grooves 212a, 212b, 212c, i.e., perpendicular to shaft axis in operation. The movement of the shank holder 211 relative to the frame 203 is realized by a groove fondled in the frame 203 and a corresponding projection on the bottom of the shank holder 211 wherein the groove and the projection cooperate with each other.

The operation will now be described with reference to FIGS. 15a to 18b.

The bone anchoring device 1" can be delivered, as described before, in the pre-assembled state with the screw element 2" being inserted and the pressure element 6" being held by crimping in such a way that its U-shaped recess is aligned with the U-shaped recess of the receiving part 5". By means of the deformed portions that protrude into the recesses of the pressure element 6", the pressure element 6" exerts a preload onto the head 4" to frictionally hold the head 4" in a certain angular position.

An additional crimping step can be applied in a case in which the friction force between the pressure element 6" and the head 4" of the pre-assembled polyaxial bone anchoring device is too low. By the additional crimping step, the surgeon or any other assistant personnel may produce a bone anchoring device with a high friction force between the pressure element 6" and the head 4". This can be done at any time before or during surgery. The additional crimping can be carried out, for example, before the screw element is screwed into the bone or after it has been screwed into the bone. The crimping tool 200 as shown in FIGS. 14a to 18b is suitable for performing the crimping before the screw element has been inserted into the bone.

Figure 15A:
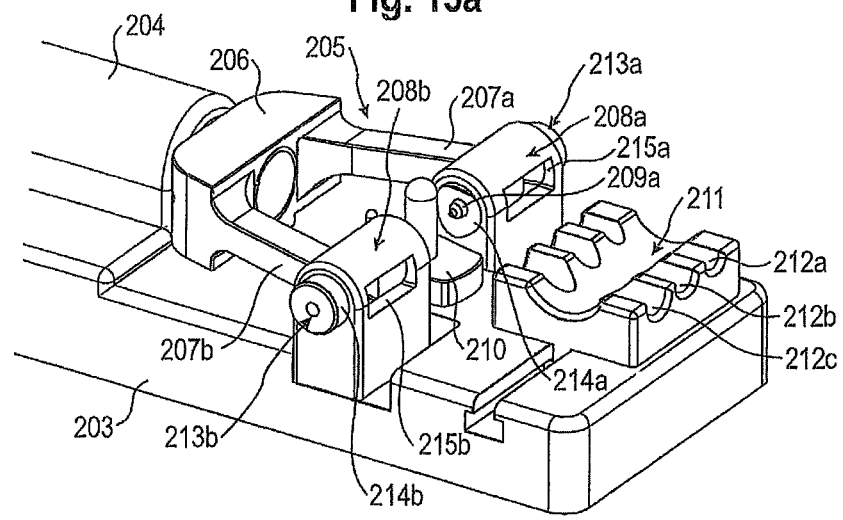
FIG. 15a shows a perspective view of the tool according to FIG. 14a in the starting position.
Figure 15B:
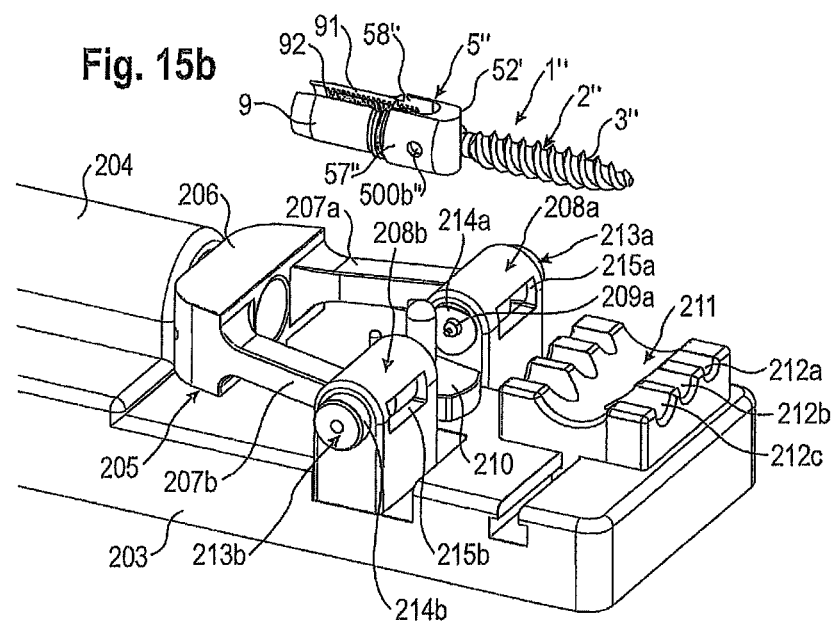
FIG. 15b shows a perspective view of the tool according to FIG. 14a in the starting position and a perspective view of the bone anchoring device.

FIG. 15a shows the crimping tool 200 in its starting position. FIG. 15b shows a step where the bone anchoring device 1" is placed in the crimping tool 200 for being crimped. FIG. 15c shows the crimping tool 200 with inserted bone anchoring element 1" before the crimping step. FIG. 15d shows the crimping position of the crimping tool 200.

First, the bone anchoring device 1" is placed in the crimping tool 200 as can be seen from FIGS. 15a, 15b, wherein the bone anchoring device 1" is positioned in that the first positioning pin 210a, the second positioning pin 210b and the third positioning pin 210c hold the receiving part 5" and thereby the bone anchoring device 1" in position as described above. The shank 2" of the bone anchoring device 1" is supported by one of the grooves 212a, 212b, 212c of the shank holder 211. The position of the shank holder 211 can be chosen depending on the shaft size. The crimping tips 209a, 209b do not yet project into the crimping bores 500a", 500b" in this starting position as can be seen from FIG. 16b.

By actuating the handle 202 and thereby actuating the lever 201 of the crimping tool 200 the actuating element 205 is moved towards the shank holder 211. Thereby, the inclined legs 207a, 207b of the actuating element 205 move towards the shank holder 211 and thereby move the tip holders 213a, 213b towards each other via the inclined planes of the legs 207a, 207b and the inclined planes of the inclined passages 216a, 216b.

Figure 17A:
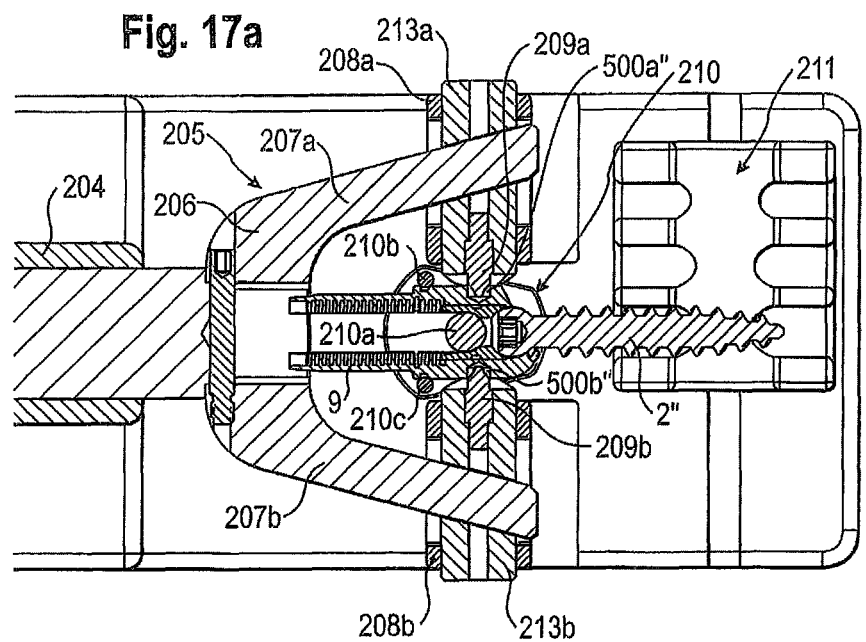
FIG. 17a shows a cross-sectional view of the tool according to FIG. 14a in an intermediate position.
Figure 17B:
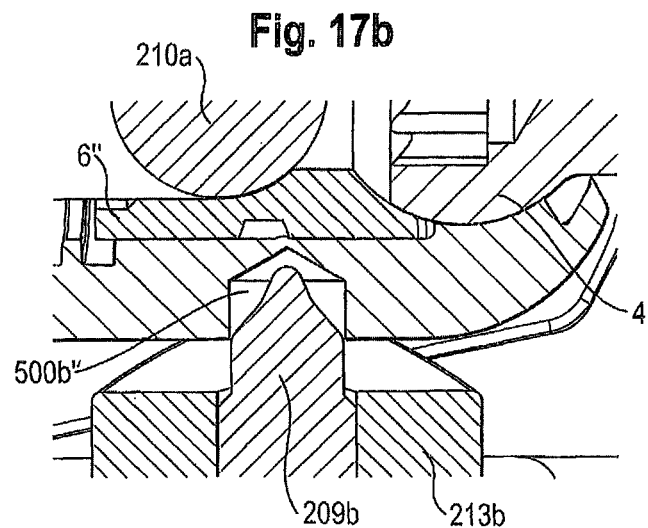
Figure 18A:
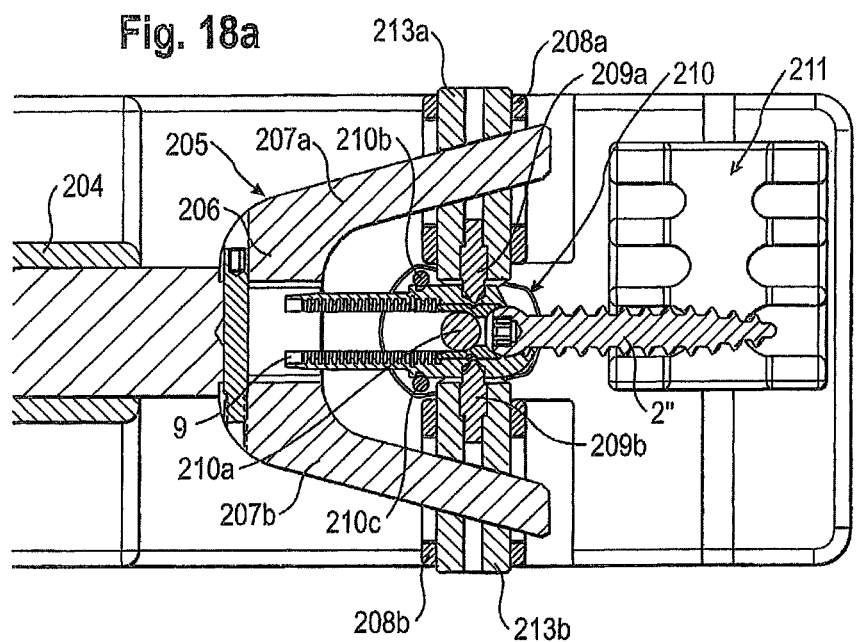
FIG. 18a shows a cross-sectional view of the tool according to FIG. 14a in the crimping position.
Figure 18B:
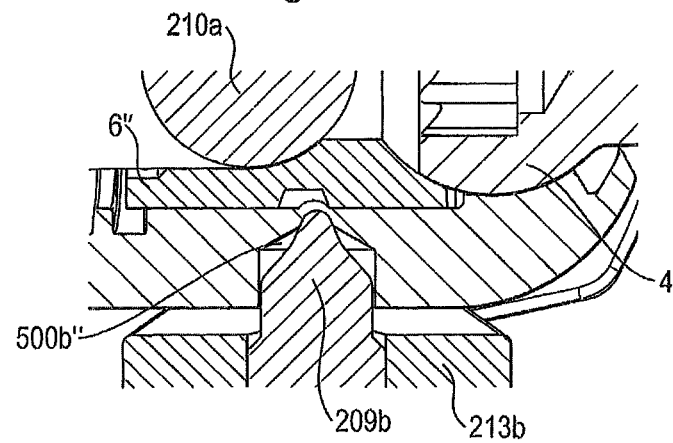

As can be seen from FIGS. 17a, 17b, the tip holders 213a, 213b holding the crimping tips 209a, 209b further move towards each other until the crimping position of the tool 200 is reached as can be seen from FIGS. 18a, 18b, where the crimping tips 209a, 209b crimp the bone anchoring device 1" in a manner described above referring to the first embodiment of the crimping tool.

Thereafter, the crimping tips 209a, 209b are retracted. The crimping process can be force-actuated and/or path-controlled. In the shown embodiment, the crimping process is path-controlled. The starting position is defined by a form-locking arrangement of the base 206 referring to the plane of the lever guiding member 204 facing the base 206 as can be seen from FIGS. 15a, 16a. The end crimping position is defined by a form-locking arrangement of a portion of the handle 202 which contacts the surface of the frame 203 as can be seen from FIG. 14b. The form-locking arrangement can be realized by a set screw which projects from the portion of the handle 202 towards the surface of the frame 203 and which contacts it in the end position of the handle 202. Thereby a precise end crimping position can be adjusted.

After the crimping tips 209a, 209b are retracted, the anchoring device 1" can be removed from the receiving part holder 210. The bone anchoring device 1" is then in a pre-assembled state with the screw element 2" being inserted and the pressure element 6" being held in such a way that it exerts a slight preload onto the head 4" which frictionally holds the head 4" in an angular position.

The crimping tool 200 can reliably produce a certain high friction force between the pressure element 6" and the head 4".

What is claimed is:

1. A crimping tool for assembling a polyaxial bone anchoring device, the crimping tool comprising:
    a tip holder having an inclined passage and comprising a crimping tip;
    an actuating member having an inclined leg; and
    a tip guide being fixedly mounted with respect to the actuating member,
    wherein the tip holder is movably guided by the tip guide,
    wherein the inclination of the inclined passage corresponds to the inclination of the inclined leg, and
    wherein the actuating member is configured to move between a first position and a second position, and the inclined leg extends farther into or farther through the tip guide in the second position than in the first position.

2. The crimping tool according to claim 1, wherein the inclined passage is cylindrical.

3. The crimping tool according to claim 1, further comprising two tip holders each having the inclined passage and comprising the crimping tip.

4. The crimping tool according to claim 3, wherein the actuating member has two inclined legs.

5. The crimping tool according to claim 3, wherein the crimping tips point at each other.

6. The crimping tool according to claim 3, wherein the inclined passages are in line with the inclined legs.

7. The crimping tool according to claim 3, further comprising a plurality of tip guides fixedly mounted with respect to the actuating member,
wherein the tip holders are movably guided by the tip guides such that the tip holders are configured to move towards each other for crimping a bone anchoring device.

8. The crimping tool according to claim 7, wherein the inclined legs are movably guided by the tip guides such that the inclined legs actuate the tip holders.

9. The crimping tool according to claim 3, wherein the crimping tips are positioned within the tip holders by a press-fit arrangement.

10. The crimping tool according to claim 1, wherein movement of the tip holder is actuated by the actuating member.

11. The crimping tool according to claim 1, wherein the actuating member is actuated by a lever.

12. The crimping tool according to claim 1, further comprising a receiving part holder for supporting a receiving part of a bone anchoring device.

13. The crimping tool according to claim 1, further comprising a shaft holder for supporting a shaft of a bone anchoring device.

14. The crimping tool according to claim 1, wherein the inclined passage extends in a first direction,
wherein the tip holder is configured to move in a second direction, and
wherein an angle between the first direction and the second direction is less than 90°.

15. The crimping tool according to claim 1, further comprising a holder comprising a positioning pin extending in a first direction,
wherein the crimping tip is configured to move along a plane in a second direction transverse to the first direction, and
wherein the positioning pin extends through the plane on which the crimping tip moves.

16. The crimping tool according to claim 15, wherein the holder further comprises second and third positioning pins each extending in the first direction and being offset from the positioning pin.

17. The crimping tool according to claim 16, wherein the positioning pin, the second positioning pin, and third positioning pin are arranged in a triangle shape.

18. The crimping tool according to claim 1, further comprising a lever configured to actuate the actuating member,
wherein a free end of the inclined leg is a different distance from an end of the inclined passage in the second position than in the first position.

19. The crimping tool according to claim 1, wherein the inclined leg extends farther into or farther through the inclined passage in the second position than in the first position.

20. The crimping tool according to claim 1, wherein the tip guide comprises a passage, the tip holder being arranged in the passage of the tip guide.

21. The crimping tool according to claim 20, wherein the passage of the tip guide extends in a first direction,
wherein the tip guide further comprises a second passage crossing the passage, and
wherein the inclined leg extends at least partially into the second passage.

22. A crimping tool for assembling a polyaxial bone anchoring device, the crimping tool comprising:
a frame;
a plurality of tip holders mounted to the frame, each of the tip holders comprising a crimping tip, the crimping tips being movable in a first direction from a first position wherein the crimping tips are spaced apart from each other to a second position wherein the crimping tips are spaced closer to each other than in the first position;
an actuating member mounted to the frame and being movable in a second direction transverse to the first direction, the actuating member configured to engage the tip holders to move the crimping tips from the first position to the second position; and
a holder mounted to the frame, the holder comprising a positioning pin having an axis extending in a third direction transverse to the first and second directions and being configured to hold a polyaxial bone anchoring device between the crimping tips,
wherein the crimping tips are arranged on a plane to be pointing at each other, the plane extending in the first and second directions,
wherein the positioning pin extends through the plane in the third direction, and
wherein the crimping tips are closer to the positioning pin in the second position than in the first position.

23. The crimping tool according to claim 22, wherein the positioning pin is arranged equidistant from the crimping tips.

* * * * *